United States Patent [19]

Miyagi et al.

[11] Patent Number: 5,465,710
[45] Date of Patent: Nov. 14, 1995

[54] ENDOSCOPE

[75] Inventors: Kunihiko Miyagi; Toshio Chikama, both of Tokyo, Japan

[73] Assignee: Machida Endoscope Co., Ltd., Tokyo, Japan

[21] Appl. No.: 238,747

[22] Filed: May 5, 1994

[30] Foreign Application Priority Data

May 12, 1993 [JP] Japan .................. 5-029560 U
May 12, 1993 [JP] Japan .................. 5-132366

[51] Int. Cl.$^6$ .................................. A61B 1/00
[52] U.S. Cl. .................. 600/139; 138/123; 604/282; 600/146
[58] Field of Search .................. 128/4, 6; 138/123, 138/127, 120; 604/282

[56] References Cited

U.S. PATENT DOCUMENTS 2,407,929  9/1946  Jeckel .................. 604/282 X
5,312,356  5/1994  Engelson et al. .................. 604/282 X

FOREIGN PATENT DOCUMENTS 60-66219  4/1985  Japan .

Primary Examiner—Richard J. Apley
Assistant Examiner—Beverly M. Flanagan
Attorney, Agent, or Firm—Fish & Richardson

[57] ABSTRACT

An endoscope suitable for inspecting a water service pipe, etc. is disclosed. The endoscope comprises an operating body and a flexible insert tube structure extending from the operating body. The insert tube structure has a flexible insert body as in a regular endoscope. The insert tube structure further has a jacket disposed on an outer periphery of the insert body and adapted to enhance a smooth reciprocal movement of the insert tube structure. The jacket is formed in a cylindrical braid by braiding a plurality of flat straps in cross-section. These straps are formed of a resin having a small friction coefficient.

11 Claims, 4 Drawing Sheets

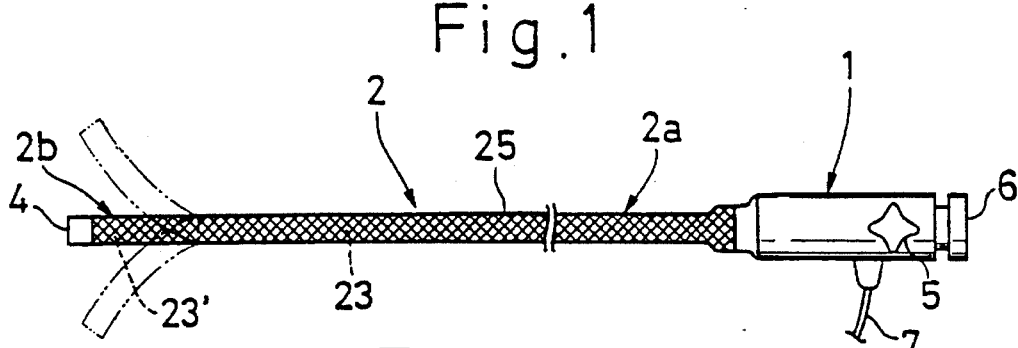
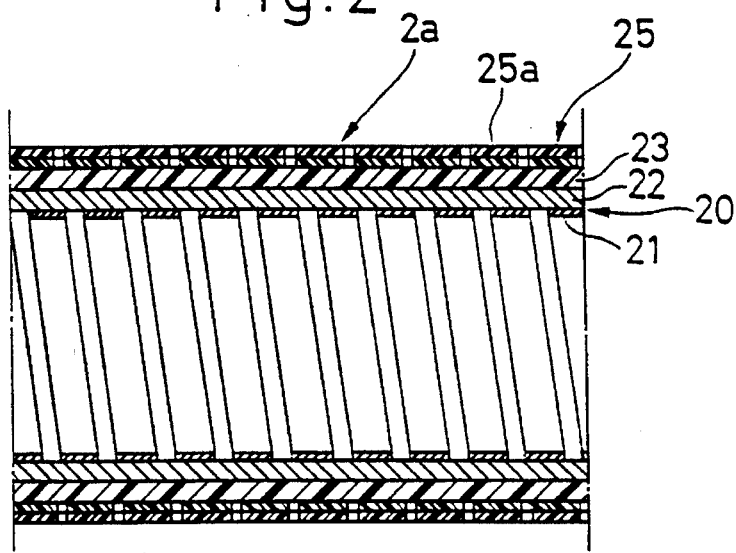
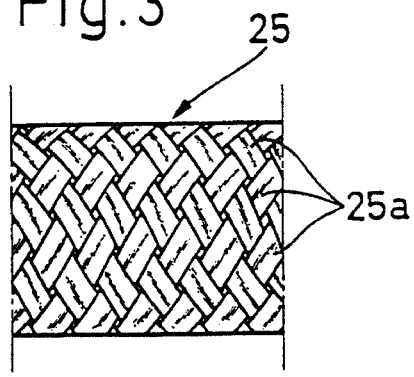
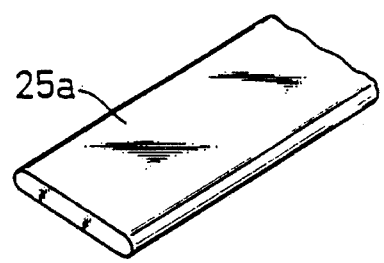
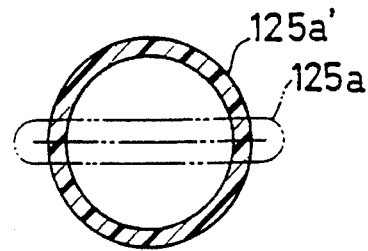
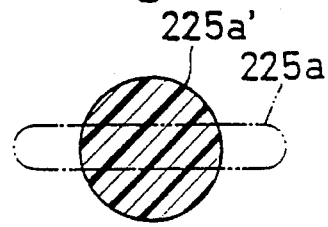

ENDOSCOPE

BACKGROUND OF THE INVENTION

This invention relates to an endoscope used for observing, for example, the inside of a piping of a water supply and drainage, and more particularly to an improvement of an insert tube structure of the endoscope.

A regular endoscope comprises an operating body and a flexible insert tube structure extending from this operating body. The insert tube structure includes a base portion occupying a large part of an entire length dimension of the insert tube structure and an angle portion extending from a distal end of the base portion and bendable by remote control from the operating body. The base portion of the insert tube structure includes a flex formed by spirally winding a metal strap plate, a cylindrical braid of metal fine wires jacketed (or placed) on an outer periphery of the flex, and a soft resin tube jacketed on an outer periphery of the braid. The angle portion of the insert tube structure includes joints rotatably connected to each other, a cylindrical braid of metal fine wires and jacketed on outer peripheries of the joints, and a soft resin tube jacketed on the braid.

In the case where the endoscope thus constructed is used for observing, for example, the inside of a piping of a water supply and drainage, the insert tube structure of the endoscope needs to have a good slidability, as well as a sufficient amount of flexibility. In the above endoscope, however, since the outer periphery of the insert tube structure is formed of a soft resin tube, slidability is bad and the soft resin tube is susceptible to scratch.

There is proposed another insert tube structure of an endoscope, as disclosed in Japanese Laid-Open Patent Application No. Sho 60-66219, in which a cylindrical braid formed of metal fine wires is additionally placed on the outer side of the resin tube as a jacket, so that the soft resin tube can be prevented from being scratched while allowing it to maintain a sufficient amount of flexibility.

However, the insert tube structure of an endoscope of the above publication has the shortcoming that since the fine wires of the jacket are readily caught by projections in the piping, it is difficult to obtain a smooth reciprocal operation of the insert tube structure in the piping. Another shortcoming had by this conventional structure is that the fine wires, which have been accidentally cut off, are occasionally liable to scratch an inner wall of the piping as well as the soft resin tube of the insert tube structure.

SUMMARY OF THE INVENTION

An object of the present invention is to provide an endoscope including a jacket, in which a smooth reciprocal movement of an insert tube structure is assured.

According to the present invention, there is provided an endoscope comprising an operating body and a flexible insert tube structure extending from the operating body, the insert tube structure comprising:

(a) a flexible insert body; and (b) a jacket disposed on an outer periphery of the insert body, the jacket being formed in a cylindrical braid by braiding a plurality of flat straps in cross-section, the straps being formed of a resin having a small friction coefficient.

BRIEF DESCRIPTION OF THE DRAWING

FIG. 1 is a side view schematically showing a whole endoscope according to one embodiment of the present invention;

FIG. 2 is an enlarged sectional view of a base portion of an insert tube structure of the endoscope of FIG. 1;

FIG. 3 is an enlarged side view of a part of a jacket of the insert tube structure of FIG. 2;

FIG. 4 is an enlarged perspective view of a strap constituting the jacket of FIG. 3;

FIG. 5 is a cross-sectional view showing a modification of the strap of FIG. 4;

FIG. 6 is a cross-sectional view showing another modification of the strap of FIG. 4;

DETAILED DESCRIPTION OF THE EMBODIMENT

Figure 7:
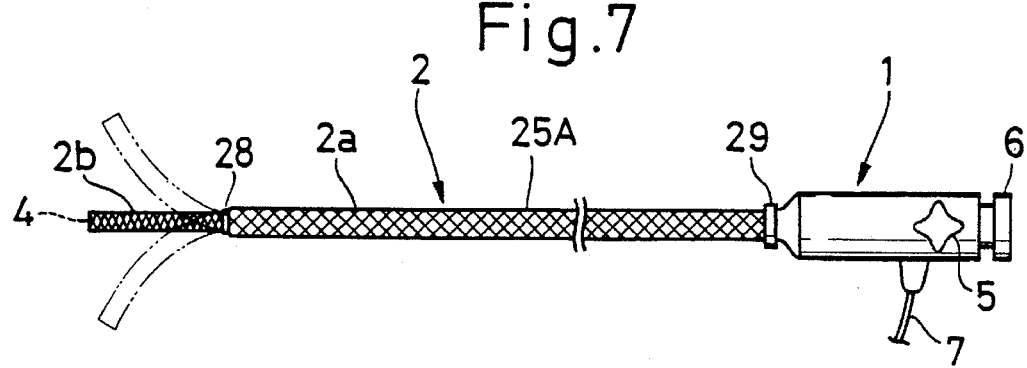
FIG. 7 is a side view schematically showing a whole endoscope according to another embodiment of the present invention.

One embodiment of the present invention will be described hereinafter with reference to the accompanying drawings. As shown in FIG. 1, an endoscope comprises an operating body 1 and a flexible insert tube structure 2 extending from a distal end of the operating body 1. The insert tube structure 2 includes a base portion 2a occupying a large part of an entire length dimension of the insert tube structure, an angle portion 2b extending from a distal end of the base portion 2a, and a hard chip 4 mounted on a distal end of the angle portion 2b. An operating member 5 is mounted on one side surface of the operating body 1, so that the angle portion 2b can be bent by the operating member 5 through a cable (not shown) extending through the insert tube structure 2. An eyepiece portion 6 is mounted on a rear end portion of the operating body 1. A light guide tube 7 extends from a lower surface (see FIG. 1) of the operating body 1. An observation window and an illumination window are formed in a front end face of the chip 4. The observation window and the eyepiece portion 6 are optically connected to each other by an image transmission optical system including a first bundle of optical fibers. The illumination window is connected to one end of a second bundle of optical fibers. The other end of the second optical fibers bundle is retained by a connector (not shown) mounted on a distal end of the light guide tube 7 via the insert tube structure 2, the operating body 1 and the light guide tube 7. The connector is connected to a light source unit.

The insert tube structure 2 of the endoscope is inserted into a piping of a water supply and drainage, or the like. Light from the light source is irradiated into the piping from the illumination window through the second optical fiber bundle. Light reflected from an inner wall of the piping is made incident from the observation window and sent to the eyepiece portion 6 through the image transmission optical system. Owing to this arrangement, the inner wall of the piping can be observed through the eyepiece portion 6.

The insert tube structure 2 includes an insert body 20 having the same construction as that of a regular endoscope. As shown in FIG. 2, the insert body 20 includes, at the base portion 2a, a flex 21 constructed by spirally winding a metal strap plate, a cylindrical braid 22 constructed by braiding metal fine wires and placed on an outer periphery of the flex 21, and a soft resin tube 23 made of a polyurethane, or the like placed on an outer periphery of the braid 22.

The insert body 20 includes, at the angle portion 2b, a plurality of joints (not shown) rotatably connected to each other, a braid (not shown) formed of metal fine wires placed on outer peripheries of the joints, and a soft resin tube 23' (FIG. 1) placed on the braid. The braid and the resin tube 23' are, respectively, higher in flexibility at the angle portion 2b than the braid 22 and the resin tube 23 at the base portion 2a. The chip 4 is attached directly to a distal end of the insert body 20 at the angle portion 2b.

The insert tube structure 2 further comprises a jacket 25 disposed on an outer periphery of the insert body 20 (i.e., on outer peripheries of the resin tubes 23 and 23'). The jacket 25 is formed in a cylindrical braid by braiding (see FIG. 3), for example, five to ten straps 25a which are flat in cross-section and rounded at opposite side portions thereof as shown in FIG. 4. As materials for forming the straps 25a, resins stronger than the resin tubes 23 and 23' and small in friction coefficient, such as, for example, PTFE (polytetrafluoroethylene), polyethylene and PA (polyamide) are preferable. A basal end of the jacket 25 is attached to the distal end of the operating body 10 or a basal end of the insert body 20 by tightening a thread or the like. A distal end of the jacket 25 is attached to a rear end of the chip 4 or the distal end of the insert body 20 likewise by tightening a thread or the like. An intermediate portion of the jacket 25 is merely left in contact with the resin tubes 23 and 23' and not secured thereto.

In the insert tube structure 2 having the above-mentioned construction, since the jacket 25 is a braid, it is not flatly or intimately contacted with the inner wall of the piping. Moreover, since the straps 25a are formed of a resin which is small in friction coefficient, their friction with the piping is small. Accordingly, since the jacket 25 can smoothly slide on the inner wall of the piping, the reciprocal movement of the insert tube structure 2 becomes very smooth in the piping. Since the jacket 25 is formed by braiding the flat straps 25a instead of the metal fine wires, it is seldom that the jacket 25 is engaged with or caught by tiny projections formed in the piping. Furthermore, since the opposite side portions of the straps 25a are rounded, the possibility can be further reduced for the jacket 25 to be engaged with or caught by the tiny projections.

Since the jacket 25 is constituted by braiding the resin straps 25a and is not in fixed relation to the resin tubes 23 and 23', flexibility of the insert tube structure 2 is not lost. Since the resin tubes 23 and 23' are covered with the jacket 23, the resin tube 23 can be prevented from being damaged when the insert tube structure 2 is reciprocally moved in the piping. Furthermore, even if the straps 25a are accidentally cut off, the cut-off edges of the straps 25a do not hurt or scratch the inner wall of the piping as well as the resin tube 23 as in the case with the metal fine wires.

As shown in FIG. 5, a resin tube 125', which has a circular configuration in section, as shown in FIG. 5, when left in a natural condition, may be used as an elongated material for braiding the jacket. When braided, the tube 125a is crushed and flattened into a flat strap 125a in cross-section as shown by an imaginary line of FIG. 5.

Alternatively, after a jacket is formed by braiding an elongated resin material 225a' of a circular cross-section as shown in FIG. 6, the material 225' may be formed into a flat strap 225a in cross-section, as shown by an imaginary line of FIG. 6, by pressing the jacket with a mandrel inserted therein, while heating the jacket from outside. It is preferable that the straps 225a intersecting one another are not welded.

Figure 8:
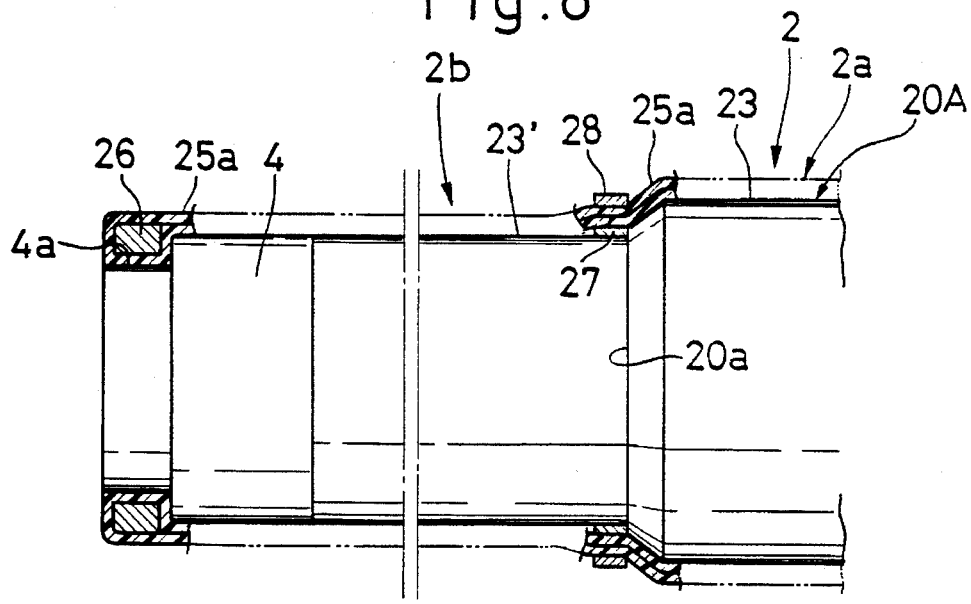
FIG. 8 is a side view, with only the jacket portion in section, showing an angle portion and a part of a base portion of an insert tube structure of the endoscope of FIG. 7.
Figure 9:
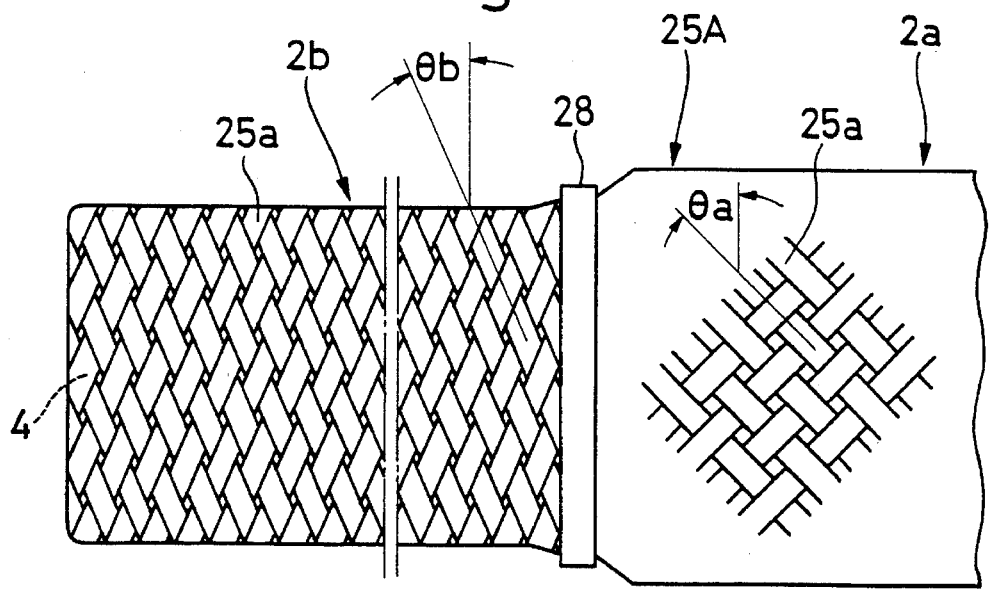
FIG. 9 is an enlarged side view of a part of the jacket at the angle portion and base portion.

FIGS. 7 to 9 shows an endoscope according to another embodiment of the present invention. In this embodiment, corresponding parts to those of the preceding embodiment are denoted by like reference numerals and detailed description thereof is omitted. This embodiment is different from the preceding embodiment in the respect that a plurality of rings are used for mounting the jacket 25A and a braiding angle of the jacket 25A is different at the base portion 2a from a braiding angle at the angle portion 2b.

More specifically, as shown in FIG. 8, an annular cut 4a is formed in an outer periphery of a distal end of the chip 4. A first ring 26 is provided on the distal end of the jacket 25A. The first ring 26 is received in the cut 4a formed in the chip 4. Intermediate portions lengthwise of the straps 25a of the jackets 25A are folded back by the first ring 26.

The insert body 20A is smaller in diameter at the angle portion 2b than the radius at the base portion 2a. A step 20a is formed on a border between the angle portion 2b and the base portion 2a. A pair of second rings 27 and 28 are disposed adjacent the step 20a. The pair of rings 27 and 28 are different in diameter, and the jacket 25A is sandwiched between the rings 27 and 28. The inner diameter of the inner second ring 27 is smaller than the outer diameter of the base portion 2a of the insert body 1. As shown in FIG. 9, the jacket 25A, when placed on the insert body 20A, is smaller in braiding angle θb (inclination angle of the strap 25a relative to a plane perpendicular to an axis of the jacket 25A) at the angle portion 2b than a braiding angle θa thereof at the base portion 2a. Also, the jacket 25A, when placed on the insert body 20A, is smaller in diameter at the angle portion 2b than its diameter at the base portion 2a.

The basal end of the jacket 25A is sandwiched between third rings 29 (only the outer ring 29 is shown in FIG. 7) having different diameters, respectively. An inner third ring is secured to the distal end of the operating body 1. This inner third ring may be secured to the basal end of the insert body 20A.

A jacket assembly comprising the jacket 25A and the rings 26, 27, 28 and 29 is separately manufactured from the insert body 20A of the endoscope. The manufacturing method will be described. The central portions of the straps 25a are folded back by the first ring 26, and the straps 25a are braided starting from the first ring 26. At this time, the braiding angle θb is small. When the straps 25a are braided upto a length generally equal to the length of the angle portion 2b, a basal end (opposite end to the first ring 26) of the braided portion is secured between the pair of second inner and outer rings 27 and 28. More specifically, after the inner and outer side surfaces of the straps 25a are etched or roughened by etching liquid, the straps 25a are secured to the second rings 27 and 28 by adhesive. The securement between the jacket 25A and the second rings 27 and 28 may be achieved merely by allowing the jacket A to be tightly sandwiched between the second rings 27 and 28. Otherwise, the securement may be achieved by connecting the rings 27 and 28 with screws, studs, etc. pierced through spaces in the braided material of the jacket 25A. After the completion of the securing operation by the second rings 27 and 28, the straps 25a are braided again upto a length Generally corresponding to the base portion 2a of the insert tube structure 2. At this time, the braiding angle θa is comparatively large. Finally, the basal end of the jacket 25A is secured by the pair of third rings 29.

While moving the jacket assembly thus manufactured in the axial direction of the insert body 20A, the jacket assembly is placed on the insert body 20A. At this time, the first ring 26 is received in the annular cut 4a of the distal end chip 4, while the inner second ring 27 is engaged with the step 20a on the border between the base portion 2a and the angle portion 2b. Then, the basal end of the jacket 25A is secured to the distal end of the operating body 1 through the third ring 29.

As described above, by receiving the first ring 26 in the cut 4a of the distal end chip 4 defining a distal end portion of the insert tube structure 2, the jacket 25A can not only be easily attached but also be correctly positioned. Since the straps 25a are folded back first by the first ring 26 when the straps 25a are braided, there is no need to firmly hold the ends of the straps 25a so that the ends will not be unbraided and the braiding operation is easy.

In the jacket 25A, since the braiding angle θb is smaller at the angle portion 2b than the braiding angle θa at the base portion 2a, the jacket 25A can be smaller in bend rigidity at the angle portion 2b than the bend rigidity at the base portion 2b.

By securing the intermediate portion of the jacket 25A, which is single in number, to the pair of second rings 27 and 28, the braiding angle can be changed at the base portion 2a from the braiding angle at the angle portion 2b. Accordingly, the manufacturing of the jacket becomes simple compared with the case where separate jackets are manufactured corresponding to the base portion and angle portion, respectively. In addition, since the second rings 27 and 28 are prohibited from moving backwardly of the step 20a, the braiding angle of the jacket 25A can be maintained small at the angle portion 2b.

In the second embodiment, the jacket 25A is secured to the operating body 1 by the third ring 29 only. This third ring 29 may be detachably attached to the operating body 1. In this case, the jacket 25A is removed after use, so that the cleaning of the insert body 20 can be performed separately from the cleaning of the jacket 25A. This constitution is convenient for the use which requires cleanliness as in the case with the observation of the inside of a piping of the water supply. This jacket 25A can easily be cleaned compared with the jacket comprising metal fine wires.

The first ring 26 used for folding back the straps may be provided on the basal end portion of the insert tube structure.

Figure 10:
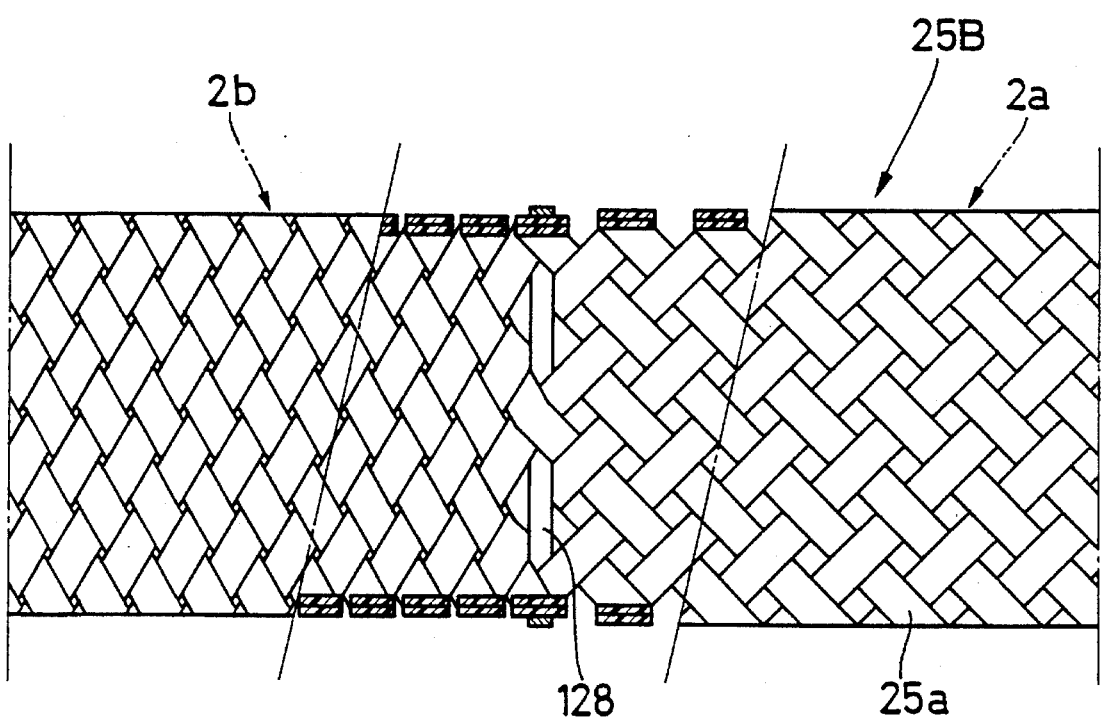
FIG. 10 is a side view, partly in section, of a modified example of the jacket.

A jacket 25B of FIG. 10 is provided with a single number of second ring 128 of a flat cross-section. This second ring 128 is incorporated into straps 25a and secured to an intermediate portion of the jacket 25B by adhesive. The second ring 128 may be secured to the jacket 25B by welding those overlapped straps 25a which are located on opposite sides of the second ring 28. The jacket 25B is placed on the insert body in the same manner as in the jacket 25A of FIGS. 7 to 9. In the stated condition of the jacket 25B placed on the insert body, the braiding angle is smaller at the angle portion 2b than a braiding angle at that portion corresponding to the base portion 2a, and the diameter is smaller at that portion corresponding to the angle portion 2b than the diameter at that portion corresponding to the base portion 2a. The second ring 128 is locked by an annular step formed on the border between the angle portion 2b and the base portion 2a of the insert body so that the second ring 128 is prohibited from moving backwardly. This embodiment is the same to the preceding embodiment in the respect that the first ring is arranged on a distal end of the jacket 25B and the third ring is arranged on a basal end thereof.

Figure 11:
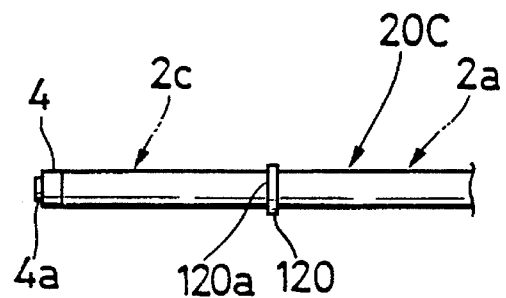
FIG. 11 is a side view showing a modified example of the insert body.

In an embodiment of FIG. 11, an annular projection 120 is formed on a border between the base portion 2a and the angle portion 2b of an insert body 20C, and a front surface of this projection 120 is served as an annular step 120a. In the insert body 20C thus constructed, the jacket 25A of FIGS. 7 to 9 and the jacket 25B of FIG. 10 can of course be used, and in addition, a jacket 25C of FIG. 12 and a jacket 25D of FIG. 13 can also be used.

Figure 12:
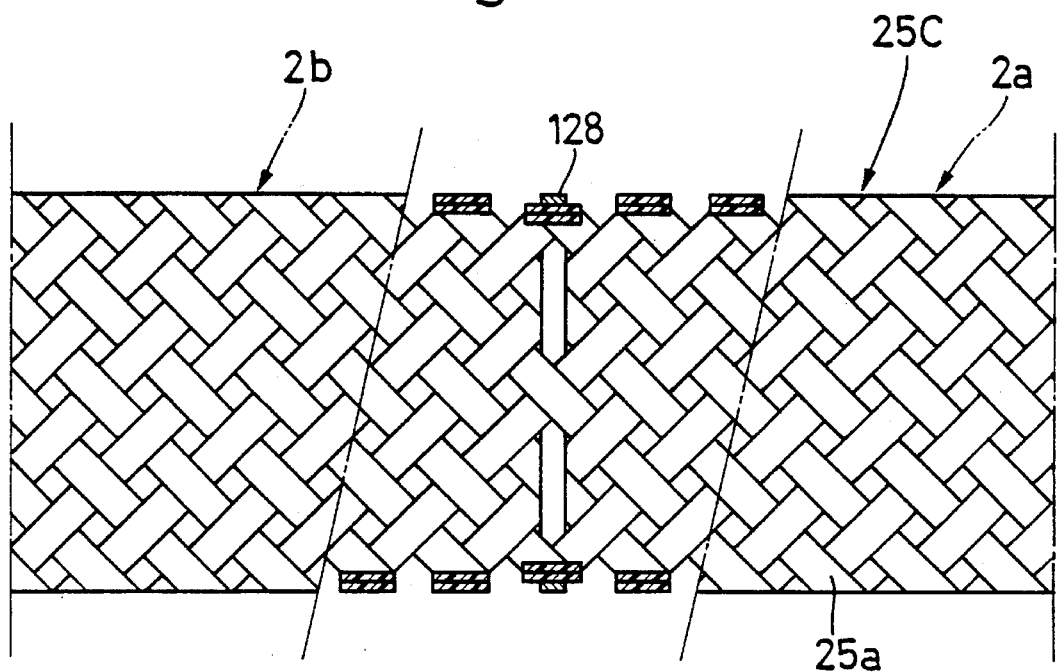
FIGS. 12 and 13 are views, like FIG. 10, showing other modified examples of the jacket, respectively.

The jacket 25C of FIG. 12 is preliminarily braided to have an equal diameter and braiding angle over the entire length. A single number of second ring 128 is fixedly braided in the jacket 25C as in the example of FIG. 10. As in the embodiment of FIGS. 7 to 9, the first ring is arranged on a distal end of the jacket 25C and the third ring is arranged on a basal end thereof.

While maintaining the original braided condition, the jacket 25C is placed on the insert body 20C. More specifically, the first ring is received in the annular cut 4a formed in the chip 4, the second ring 128 is engaged with the step 120a of the projection 120 so that the second ring 128 is prohibited from moving backwardly, and only the third ring is secured to a basal portion of the insert body 20C or to a distal end of the operating body. In this case, the jacket 25C is equal in braiding angle at the base portion 2a to the braiding angle at the angle portion 2b. Since the second ring 128 is prohibited from moving backwardly, the length of the angle portion 2a of the jacket 25 is not increased and the braiding angle is prohibited from becoming larger at this area.

An arrangement is also possible in which the jacket 25C is preliminarily braided to have a shorter base portion 2a than the base portion 2a of the insert body 20C, and when the jacket 25C is placed on the insert body 20, the basal end of the jacket 25C is pulled while maintaining the condition of the second ring 128 engaged with the step 120a, so that the braiding angle is increased while reducing the diameter of the jacket 25C at the base portion 2a.

Figure 13:
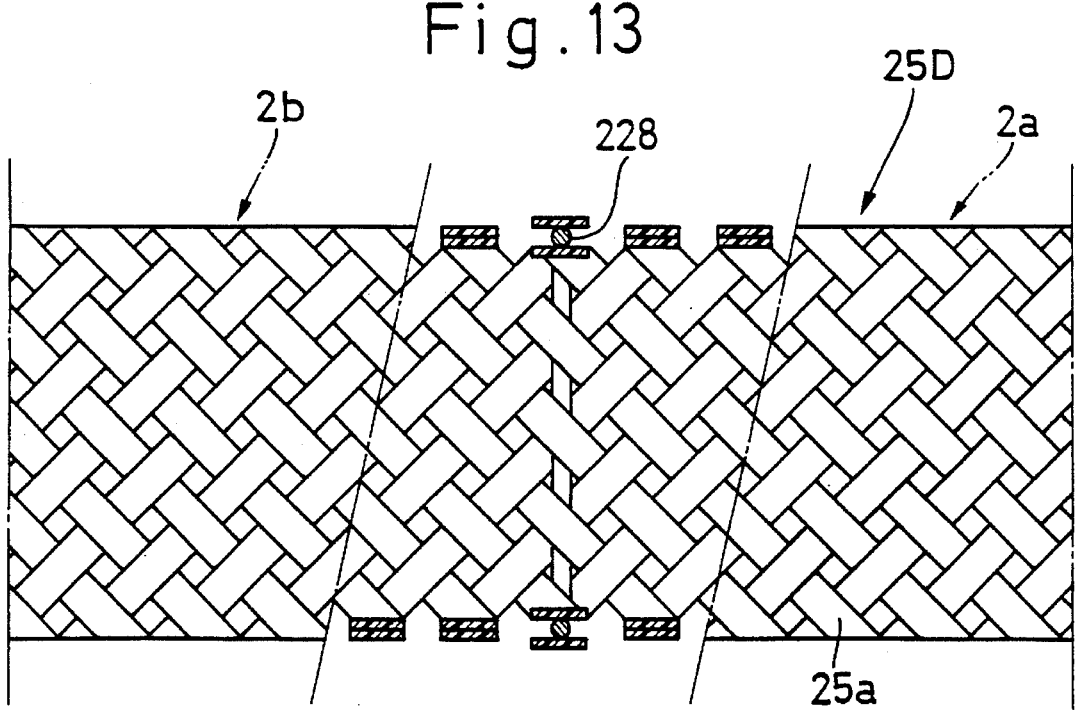

The jacket 25D of FIG. 13 is the same in construction as the jackets 25B and 25C of FIGS. 10 and 12, except that a circular second ring 228 in section is used.

The present invention is not limited to the above embodiments, and various changes can be made. For example, instead of forming the annular step on the border between the base portion and the angle portion of the insert body, a single or a pair of second rings are secured to this border by adhesive or the like. Also, the jacket and the insert body may be secured to each other at the border between the base portion and the angle portion without using any rings.

The opposite side portions of the straps are not necessarily rounded. In other words, they may be rectangular in section.

The endoscope may be provided on the observation window with an image sensor (CCD). In this case, the image transmission means comprises signal wires extending through the insert tube structure.

The outer periphery of the insert body of the endoscope may be formed of a metal braid. In this case, the jacket of the present invention is jacketed on the metal braid.

What is claimed is:

1. An endoscope comprising an operating body and a flexible insert tube structure extending from said operating body, said insert tube structure comprising:

(a) a flexible insert body; and (b) a jacket disposed on an outer periphery of said insert body, said jacket being formed in a cylindrical braid by braiding a plurality of straps which are flat in cross-section, said straps being formed of a resin having a small coefficient of friction, in which an intermediate portion of said straps is folded back at a ring disposed at one end of said jacket, to thereby incorporate said ring in said one end of said jacket.

2. An endoscope comprising an operating body and a flexible insert tube structure extending from said operating body, said insert tube structure comprising:

(a) a flexible insert body; and (b) a jacket disposed on an outer periphery of said insert body, said jacket being formed in a cylindrical braid by braiding a plurality of straps which are flat in cross-section, said straps being formed of a resin having a small coefficient of friction, in which an intermediate portion of said straps is folded back at a ring disposed at one end of said jacket, said insert tube structure further comprises a chip provided on a distal end of said insert body, an annular cut being formed in an outer periphery of a distal end portion of said chip and said ring being fitted in said cut.

3. An endoscope comprising an operating body and a flexible insert tube structure extending from said operating body, said insert tube structure comprising:

(a) a flexible insert body; and (b) a jacket disposed on an outer periphery of said insert body, said jacket being formed in a cylindrical braid by braiding a plurality of straps which are flat in cross-section, said straps being formed of a resin having a small coefficient of friction, in which said insert body includes a base portion extending from said operating body and occupying a large portion of an entire length dimension of said insert body, and an angle portion extending from a distal end of said base portion and bendable by remote control from said operating body, said straps extending over said base portion and angle portion of said insert body, ring means being secured to that part of said jacket which is located on a border between said base portion and said angle portion.

4. An endoscope according to claim 3, in which said ring means includes a pair of rings, said that part of said jacket which is located on the border between said base portion and said angle portion being sandwiched between said pair of rings.

5. An endoscope according to claim 3, in which said ring means comprises a single number of ring, said ring being fixedly incorporated in said that part of said jacket which is located on the border between said base portion and said angle portion.

6. An endoscope according to claim 3, in which a braiding condition of said jacket is different at that area corresponding to said angle portion from a braiding condition thereof but at that area corresponding to said base portion.

7. An endoscope according to claim 6, in which a braiding angle of said jacket being smaller at that area corresponding to said angle portion than a braiding angle of said jacket at that area corresponding to said base portion, said braiding angle being an angle of inclination of said straps with respect to a plane perpendicular to an axis of said jacket.

8. An endoscope according to claim 3, in which an annular step is formed on the border between said angle portion and said base portion, said ring means being engaged with said annular step so that said ring means is prohibited from moving backwardly.

9. An endoscope according to claim 8, in which the radius of said angle portion is smaller than that of said base portion, so that said annular step is formed between said angle portion and said base portion.

10. An endoscope according to claim 8, in which an annular projection is formed between said angle portion and said base portion, so that a front surface of said projection is served as said annular step.

11. An endoscope comprising an operating body and a flexible insert tube structure extending from said operating body, said insert tube structure comprising:

(a) a flexible insert body; and (b) a jacket disposed on an outer periphery of said insert body, said jacket being formed in a cylindrical braid by braiding a plurality of straps which are flat in cross-section, said straps being formed of a resin having a small coefficient of friction coefficient, in which said insert body includes a base portion extending from said operating body and occupying a large portion of an entire length dimension of said insert body, and an angle portion extending from a distal end of said base portion and bendable by remote control from said operating body, said straps of said jacket extending over said base portion and angle portion, said jacket being secured to the border between said base portion and said angle portion.

* * * * *